US006916464B2

(12) United States Patent
Hansenne et al.

(10) Patent No.: US 6,916,464 B2
(45) Date of Patent: Jul. 12, 2005

(54) SUNSCREEN COMPOSITIONS

(75) Inventors: Isabelle Hansenne, Westfield, NJ (US);
Anil Shah, East Windsor, NJ (US);
Angelike Galdi, Westfield, NJ (US)

(73) Assignee: L'Oreal, Paris (FR)

( * ) Notice: Subject to any disclaimer, the term of this patent is extended or adjusted under 35 U.S.C. 154(b) by 70 days.

(21) Appl. No.: 10/323,649

(22) Filed: Dec. 20, 2002

(65) Prior Publication Data

US 2004/0126336 A1 Jul. 1, 2004

(51) Int. Cl.⁷ .................... A61K 7/42; A61K 7/00; A61K 31/74
(52) U.S. Cl. .................. 424/59; 424/60; 424/78.02; 424/78.08; 424/400; 424/401
(58) Field of Search ............... 424/59, 60, 78.02, 424/78.08, 400, 401

(56) References Cited

U.S. PATENT DOCUMENTS

| | | | |
|---|---|---|---|
| 2,823,195 A | 2/1958 | Shorr et al. | |
| 3,723,566 A | 3/1973 | Thompson et al. | |
| 4,322,400 A | 3/1982 | Yuhas | |
| 5,262,505 A | 11/1993 | Nakashima et al. | |
| 5,407,986 A | 4/1995 | Furukawa et al. | |
| 5,412,004 A | 5/1995 | Tachibana et al. | |
| 5,473,041 A | 12/1995 | Itoh | |
| 5,567,428 A | 10/1996 | Hughes | |
| 5,837,223 A | 11/1998 | Barone et al. | |
| 5,874,069 A | 2/1999 | Mendolia et al. | |
| 5,919,441 A | 7/1999 | Mendolia et al. | |
| 5,981,680 A | 11/1999 | Petroff et al. | |
| 6,051,216 A | 4/2000 | Barr et al. | |
| 6,060,072 A | 5/2000 | Konik et al. | |
| 6,103,250 A | 8/2000 | Brieva et al. | |
| 6,353,076 B1 | 3/2002 | Barr et al. | |
| 6,362,287 B1 | 3/2002 | Chorvath et al. | |
| 6,362,288 B1 | 3/2002 | Brewer et al. | |
| 6,423,324 B1 | 7/2002 | Murphy et al. | |
| 6,426,062 B1 | 7/2002 | Chopra et al. | |
| 6,451,295 B1 * | 9/2002 | Cai et al. ................ | 424/65 |
| 6,503,632 B1 | 1/2003 | Hayashi et al. | |
| 6,569,955 B1 | 5/2003 | Brewer et al. | |
| 2002/0048557 A1 | 4/2002 | Cai et al. | |
| 2003/0068348 A1 | 4/2003 | Ferrari et al. | |
| 2003/0072730 A1 | 4/2003 | Tournilhac | |
| 2003/0082129 A1 | 5/2003 | Buckingham et al. | |
| 2003/0170188 A1 | 9/2003 | Ferrari et al. | |

FOREIGN PATENT DOCUMENTS

| | | |
|---|---|---|
| EP | 0 377 447 A2 | 7/1990 |
| EP | 0 693 517 A1 | 1/1996 |
| EP | 0 923 928 | 6/1999 |
| EP | 1 048 686 | 11/2000 |
| EP | 1 068 856 | 1/2001 |
| FR | 2 765 800 | 1/1999 |
| GB | 134 8783 | 3/1974 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO 01/09239 A1 | 2/2001 |
| WO | WO 01/97758 A2 | 12/2001 |
| WO | WO 02/089760 A1 | 11/2002 |
| WO | WO 03/013447 A2 | 2/2003 |
| WO | WO 03/105788 A2 | 6/2003 |

OTHER PUBLICATIONS

Dow Corning® 2–8176 Gellant, Aug. 2002 Product Launch (20 pp.).
Dow Corning® 2–8178 Gellant, Ref. No. 27–1055–01, Aug. 2002, 35 pp.
Dow Corning® 2–8178 Gellant, Product Information Personal Care, 6 pp.
Shin–Etsu Silicones for Personal Care; Product Brochure, KSP–100–101–102–103–104–105 "Hybrid Silicone Powders for Personal Care".
Shin–Etsu Silicones for Personal Care; Product Brochure, KSP–200–300 "Hybrid Silicone Powders containing Fluoroalkyl or Phenyl group for Personal Care".

* cited by examiner

*Primary Examiner*—Shelley A. Dodson
(74) *Attorney, Agent, or Firm*—Oblon, Spivak, McClelland, Maier & Neustadt, P.C.

(57) ABSTRACT

The present invention relates to improved sunscreen compositions, more preferably to improve sunscreen compositions containing at least one sunscreening agent (sunscreen) and a silicone-polyamide copolymer.

18 Claims, No Drawings

SUNSCREEN COMPOSITIONS

FIELD OF THE INVENTION

The present invention relates to improved sunscreen compositions, more particularly to improved compositions containing at least one sunscreening agent (sunscreen). In a preferred embodiment, the invention compositions comprise a silicone-polyamide copolymer. While the invention compositions may take any form, they preferably are in the form of a gel or an emulsion (O/W, W/O, triple emulsion, etc.). In a preferred embodiment, the invention compositions comprise at least one sunscreen, a nylon-611/dimethicone copolymer and, optionally, PPG-3 myristyl ether. In a highly preferred embodiment, the composition of the invention contains a nylon-611/dimethicone copolymer in an amount that maintains or improves the sun protection factor (SPF) of the composition. In a preferred embodiment the invention compositions, particularly when in the form of alcoholic gels, provide waterproof compositions with pleasant aesthetics and no pilling.

BACKGROUND OF THE INVENTION

Compositions containing sunscreens are highly popular. One problem with such sunscreen-containing compositions, however, is the provision of a high SPF factor (e.g., 30+), especially when the composition contains alcohol. As will be shown in further detail below, the present inventors have found that the use of a silicone-polyamide copolymer, preferably a nylon-611/dimethicone copolymer and, optionally, PPG-3 myristyl ether alleviates such problems and can, in fact, increase quite significantly the SPF factor of a composition as compared to the same composition absent the copolymer.

DETAILED DESCRIPTION OF THE PRESENT INVENTION

The present invention compositions may be of any form, and are particularly preferably in the form of a gel or an emulsion. The invention compositions preferably, but do not necessarily, contain at least one alcohol. Examples of such alcohols include ethanol, propanol, butanol, etc., preferably $C_2$–$C_8$ alcohols. The amount of such alcohol may vary from a minor amount, for example 0.1% based on total weight of composition, to a major amount (for example, 30% and more based on total weight).

Preferred gel compositions according to the invention preferably comprise, e.g., UV filters, alcohols, oils, thickeners (e.g., celluloses), optionally water.

Preferred emulsions according to the invention preferably comprise at least one emulsifier selected from the group consisting of amphoteric, anionic, cationic or nonionic emulsifiers, used alone or as a mixture, and optionally a coemulsifier. The emulsifiers are preferably chosen according to the emulsion to be obtained (W/O or O/W). The emulsifier and the coemulsifier are generally preferably present in the composition in a proportion ranging from 0.3 to 30% by weight and preferably from 0.5 to 20% by weight with respect to the total weight of the composition.

Mention may be made, for the W/O emulsions, for example, as emulsifiers, of dimethicone copolyols, such as the mixture of cyclomethicone and of dimethicone copolyol sold under the name "DC 5225 C" by Dow Corning, and alkyl dimethicone copolyols, such as the laurylmethicone copolyol sold under the name "Dow Corning 5200 Formulation Aid" by Dow Corning and the cetyl dimethicone copolyol sold under the name Abil EM 90$^R$ by Goldschmidt. Use may also be made, as surfactant of W/O emulsions, of a crosslinked solid organopolysiloxane elastomer comprising at least one oxyalkylenated group, such as those obtained according to the procedure of Examples 3, 4 and 8 of the document U.S. Pat. No. 5,412,004 and the examples of the document U.S. Pat. No. 5,811,487, in particular the product of Example 3 (synthetic example) of Patent U.S. Pat. No. 5,412,004, and such as that sold under the reference KSG 21 by Shin Etsu. Use may also be made, as emulsifier, of a polyolefin-derived oligomer or polymer comprising a succinic ending; the latter is preferably a polyolefin comprising an esterified or amidated succinic ending or a salt of such a polyolefin and in particular polyisobutylene comprising an esterified or amidated succinic ending such as the products sold under the names L5603 and L2721 and OS131769 by Lubrizol.

Mention may be made, for the O/W emulsions, for example, as emulsifiers, of nonionic emulsifiers, such as esters of fatty acids and of glycerol which are oxyalkylenated (more particularly polyoxyethylenated); esters of fatty acids and of sorbitan which are oxyalkylenated; esters of fatty acids which are oxyalkylenated (oxyethylenated and/or oxypropylenated); ethers of fatty alcohols which are oxyethylenated (oxyethylenated and/or oxypropylenated); sugar esters, such as sucrose stearate; and their mixtures, such as the mixture of glyceryl stearate and of PEG-40 stearate.

When the composition according to the invention comprises an oily phase, the latter preferably comprises at least one oil. It can additionally comprise other fatty substances.

Mention may be made, as oils which can be used in the composition of the invention, of, for example:

hydrocarbonaceous oils of animal origin, such as perhydrosqualene;

hydrocarbonaceous oils of vegetable origin, such as liquid triglycerides of fatty acids comprising from 4 to 10 carbon atoms, such as triglycerides of heptanoic acid or octanoic acid, or alternatively, for example, sunflower, maize, soybean, gourd, grape seed, sesame, hazelnut, apricot, macadamia, arara, castor or avocado oils, triglycerides of caprylic/capric acids, such as those sold by Stéarineries Dubois or those sold under the names Miglyol 810, 812 and 818 by Dynamit Nobel, jojoba oil, or karite butter oil;

synthetic esters and ethers, in particular of fatty acids, such as the oils of formulae $R^1COOR^2$ and $R^1OR^2$ in which $R^1$ represents the residue of a fatty acid comprising from 8 to 29 carbon atoms and $R^2$ represents a branched or unbranched hydrocarbonaceous chain comprising from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as volatile or nonvolatile liquid paraffins and their derivatives, liquid petrolatum, polydecenes or hydrogenated polyisobutene, such as parleam oil;

fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol; partially hydrocarbon-comprising and/or silicone-comprising fluorinated oils, such as those disclosed in the document JP-A-2-295912;

silicone oils, such as volatile or nonvolatile polymethyl-siloxanes and polydimethylsiloxanes (PDMS) comprising a linear or cyclic silicone chain which are liquid or pasty at ambient temperature, in particular cyclopolydimethylsiloxanes (cyclomethicones), such as cyclohexasiloxane; polydimethylsiloxanes comprising pendent alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyltrimethylsiloxydiphenylsiloxanes, diphenyl dimethicones, diphenylmethyldiphenyltrisiloxanes, (2-phenylethyl) trimethylsiloxysilicates and polymethylphenylsiloxanes;

their mixtures.

The term "hydrocarbonaceous oil" is understood to mean, in the list of the oils mentioned above, any oil predominantly comprising carbon and hydrogen atoms and optionally ester, ether, fluorinated, carboxylic acid and/or alcohol groups.

The other fatty substances which can be present in the oily phase are, for example, fatty acids comprising from 8 to 30 carbon atoms, such as stearic acid, lauric acid, palmitic acid and oleic acid; waxes, such as lanolin, beeswax, carnauba or candelilla wax, paraffin or lignite waxes or microcrystalline waxes, ceresin or ozokerite, or synthetic waxes, such as polyethylene waxes or Fischer-Tropsch waxes; silicone resins, such as trifluoromethyl $C_{1-4}$ alkyl dimethicone and trifluoropropyl dimethicone; and silicone elastomers, such as the products sold under the names "KSG" by Shin-Etsu, under the names "Trefil", "BY29" or "EPSX" by Dow Corning or under the names "Gransil" by Grant Industries.

These fatty substances can be chosen in a way varied by a person skilled in the art in order to prepare a composition having the desired properties, for example of consistency or of texture, without undue hardship.

According to a specific embodiment of the invention, the composition according to the invention is a water-in-oil (W/O) or oil-in-water (O/W) emulsion. The proportion of the oily phase in the emulsion may preferably range from 5 to 80% by weight and preferably from 5 to 50% by weight with respect to the total weight of the composition.

As noted above, the compositions in accordance with the invention comprise at least one sunscreen such as an organic sunscreen and/or an inorganic sunscreen which is preferably active in the UV-A and/or UV-B regions (absorbers), and which can be soluble in water or in fats or insoluble in, e.g., cosmetic solvents commonly used. The sunscreens which may be used according to the present invention preferably comprise chemical absorbers, but may also comprise physical blockers. Typically combinations of one of more sunscreens may be used.

Organic sunscreens useful herein include anthranilates; cinnamic derivatives; dibenzoylmethane derivatives; salicylic derivatives; camphor derivatives; triazine derivatives, such as those disclosed in Patent Applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benzimidazole derivatives; imidazolines; bisbenzoazolyl derivatives as disclosed in Patents EP 669 323 and U.S. Pat. No. 2,463,264; p-aminobenzoic acid (PABA) derivatives; methylenebis (hydroxyphenylbenzotriazole) derivatives as disclosed in Applications U.S. Pat. Nos. 5,237,071, 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; 4,4-diarylbutadienes as disclosed in Applications EP 0 967 200, DE 197 46 654, DE 197 55 649, EP-A-1 008 586, EP 1 133 980 and EP 133 981; and their mixtures.

By way of illustration, mention may be made, as sunscreens which are generally active in the UV-A and/or UV-B regions, denoted below under their INCI names, of:

p-aminobenzoic acid (PABA) derivatives, in particular PABA, ethyl PABA, ethyl dihydroxypropyl PABA, ethylhexyl dimethyl PABA (sold in particular under the name "Escalol 507" by ISP), glyceryl PABA or PEG-25 PABA (sold under the name "Uvinul P25" by BASF), salicylic derivatives, in particular homosalate (sold under the name "Eusolex HMS" by Rona/EM Industries), ethylhexyl salicylate (sold under the name "Neo Heliopan OS" by Haarmann and Reimer), dipropylene glycol salicylate (sold under the name "Dipsal" by Scher), or TEA salicylate (sold under the name "Neo Heliopan TS" by Haarmann and Reimer), dibenzoylmethane derivatives, in particular butyl methoxydibenzoylmethane (sold in particular under the trade name "Parsol 1789" by Hoffmann-LaRoche), or isopropyl dibenzoylmethane, cinnamic derivatives, in particular ethylhexyl methoxycinnamate (sold in particular under the trade name "Parsol MCX" by Hoffmann-LaRoche), isopropyl methoxycinnamate, isoamyl methoxycinnamate (sold under the trade name "Neo Heliopan E 1000" by Haarmann and Reimer), cinoxate, DEA methoxycinnamate, diisopropyl methyl cinnamate, or glyceryl ethylhexanoate dimethoxycinnamate, β,β-diphenylacrylate derivatives, in particular octocrylene (sold in particular under the trade name "Uvinul N539" by BASF) or etocrylene. (sold in particular under the trade name "Uvinul N35" by BASF), benzophenone, in particular benzophenone-1 (sold under the trade name "Uvinul 400" by BASF), benzophenone-2 (sold under the trade name "Uvinul D50" by BASF), benzophenone-3 or oxybenzone (sold under the trade name "Uvinul M40" by BASF), benzophenone-4 (sold under the trade name "Uvinul MS40" by BASF), benzophenone-5, benzophenone-6 (sold under the trade name "Helisorb 11" by Norquay), benzophenone-8 (sold under the trade name "Spectra-Sorb UV-24" by American Cyanamid), benzophenone-9 (sold under the trade name "Uvinul DS-49" by BASF), benzophenone-12, or n-hexyl 2-(4-diethylamino-2-hydroxybenzoyl)benzoate, benzylidene camphor derivatives, in particular 3-benzylidene camphor (manufactured under the name "Mexoryl SD" by Chimex), 4-methylbenzylidene camphor (sold under the name "Eusolex 6300" by Merck), benzylidene camphor sulphonic acid (manufactured under the name "Mexoryl SL" by Chimex), camphor benzalkonium methosulphate (manufactured under the name "Mexoryl SO" by Chimex), terephthalylidene dicamphor sulphonic acid (manufactured under the name "Mexoryl SX" by Chimex), or polyacrylamidomethyl benzylidene camphor (manufactured under the name "Mexoryl SW" by Chimex), benzimidazole derivatives, in particular phenylbenzimidazole sulphonic acid (sold in particular under the trade name "Eusolex 232" by Merck), or disodium phenyl dibenzimidazole tetrasulphonate (sold under the trade name "Neo Heliopan AP" by Haarmann and Reimer), triazine derivatives, in particular anisotriazine (sold under the trade name "Tinosorb S" by Ciba Specialty Chemicals), ethylhexyl triazone (sold in particular under the trade name "Uvinul T150" by BASF), diethylhexyl butamido triazone (sold under the trade name "Uvasorb HEB" by Sigma 3V) or 2,4,6-tris(diisobutyl 4'-amino-benzalmalonate)-s-triazine, benzotriazole derivatives, in particular drometrizole trisiloxane (sold under the name "Silatrizole" by Rhodia Chimie) or methylene bisbenzotriazolyl tetramethylbutylphenol (sold in the solid form under the trade name "Mixxim BB/100" by Fairmount Chemical or in the micronized form in aqueous dispersion under the trade name "Tinosorb M" by Ciba Specialty Chemicals), anthranilic derivatives, in particular menthyl anthranilate (sold under the trade name "Neo Heliopan MA" by Haarmann and Reimer), imidazoline derivatives, in particular ethylhexyl dimethoxybenzylidene dioxoimidazoline propionate, benzalmalonate derivatives, in particular polyorganosiloxane comprising benzalmalonate functional groups (sold under the trade name "Parsol SLX" by Hoffmann-LaRoche), 4,4-diarylbutadiene derivatives, in particular 1,1'-dicarboxy (2,2'-dimethylpropyl)-4,4-diphenylbutadiene, and their mixtures.

Organic sunscreens which are quite useful herein include those selected from the group consisting of ethylhexyl salicylate, ethylhexyl methoxycinnamate, octocrylene, phenylbenzimidazole sulphonic acid, benzophenone-3, benzophenone4, benzophenone-5, 4-methylbenzylidene camphor, terephthalylidene dicamphor sulphonic acid, disodium phenyl dibenzimidazole tetrasulphonate, 2,4,6-tris (diisobutyl 4'-aminobenzalmalonate)-s-triazine, anisotriazine, ethylhexyl triazone, diethylhexyl butamido triazone, methylene bisbenzotriazolyl tetramethylbutylphenol, drometrizole trisiloxane, 1,1'-dicarboxy (2,2'-dimethylpropyl)-4,4-diphenylbutadiene, and their mixtures.

The inorganic sunscreens may be selected from the group consisting of pigments or alternatively nanopigments (mean size of the primary particles: generally between 5 nm and 100 run, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments, which are all UV sunscreens well known per se. Conventional coating agents are, furthermore, alumina and/or aluminium stearate. Such nanopigments formed from coated or uncoated metal oxides are disclosed in particular in Patent Applications EP 518 772 and EP 518 773.

Another group of preferred sunscreens according to this invention are certain UV-A and UV-B absorbers. Classifying the chemical absorbers generally as UV-A or UV-B absorbers is accepted within the industry. However, a more precise classification is one based upon the chemical properties of the sunscreens. There are eight major classifications of sunscreen chemical properties which arc discussed at length in "Sunscreens—Development, Evaluation and Regulatory Aspects," by N. Shaath et al., 2nd. Edition, pages 269–273, Marcel Dekker, Inc. (1997). This discussion, in its entirety, is incorporated by reference herein.

Preferred UV-A absorbers generally absorb radiation in the 320 to 400 nm region of the ultraviolet spectrum. Such preferred UV-A absorbers include anthranilates, benzophenones, and dibenzoyl methanes. Preferred UV-B absorbers generally absorb radiation in the 280 to 320 nm region of the ultraviolet spectrum. Such preferred UV-B absorbers include p-aminobenzoic acid derivatives, camphor derivatives, cinnamates, and salicylates. Useful sunscreens active in the UV-A and/or UV-B range also include:

p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate ate,
3-(4'-trimethylammunium)-benzyliden-bornan-2-one methylsulfate,
2-hydroxy-4-methoxybenzophenone,
2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy4-methoxy-4'-methoxybenzophenone,
-(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,1-camphor,
3-benzylidene-d,1-camphor,
benzene 1,4-di(3-methylidene-10-camphosulfonic) acid and salts thereof (the product Mexoryl SX described in U.S. Pat. No. 4,585,597 issued to Lange et al. on Apr. 29, 1986),
urocanic acid,
2,4,6-tris[p-(2'-ethylhexyl-1'-oxycarbonyl)-anilino]-1,3,5-triazine,
2-[(p-(tertiobutylamido)anilino]-4,6-bis-[(p-(2'-ethylhexyl-1'-oxycarbonyl)anilino]-1,3,5-triazine,
2,4-bis{[4-(2-ethyl-hexyloxy)]-2-hydroxy]-phenyl}-6-(4-methoxy-phenyl)-1,3,5-triazine ("TINOSORB S" marketed by Ciba),
the polymer of N-(2 et 4)-[(2-oxoborn-3-yliden)methyl] benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane),
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that marketed under the trademark TINOSORB M by Ciba-Geigy, and solubilized 2,2'-methylene-bis-[6-(2H-benzotriazol-2-yl)-4-(methyl)phenol] such as that marketed under the trademark MIXXIM BB/200 by Fairmount Chemical.

The dibenzoyl methane derivatives other than avobenzone are described, for example, in FR-2,326,405, FR-2,440,933 and EP-0,114,607, hereby expressly incorporated by reference.

Other dibenzoyl methane sunscreens other than avobenzone include (whether singly or in any combination):

2-methyldibenzoylmethane
4-methyldibenzoylmethane
4-isopropyldibenzoylmethane
4-tert.-butyldibenzoylmethane
2,4-dimethyldibenzoylmethane
2,5-dimethyldibenzoylmethane
4,4'-diisopropyldibenzoylmethane
4,4'-dimethoxydibenzoylmethane
2-methyl-5-isopropyl-4'-methoxydibenzoylmethane
2-methyl-5-tert.-butyl-4'-methoxydibenzoylmethane
2,4-dimethyl4'-methoxydibenzoylmethane
2,6-dimethyl-4-tert.-butyl-4'-methoxydibenzoylmethane Particularly useful sunscreens which may be formulated into the compositions of the present invention include chemical absorbers such as p-aminobenzoic acid derivatives, anthranilates, benzophenones, camphor derivatives, cinnamic derivatives, dibenzoyl methanes (such as avobenzone also known as Parsol®1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP-0,863,145, EP-0,517,104, EP-0,570,838, EP-0,796,851, EP-0,775,698, EP-0,878,469, EP-0,933,376, EP-0,893,119, EP-0,669,323, GB-2,303,549, DE-1,972,184 and WO-93/04665, also expressly incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens all of which are useful herein is described in U.S. Pat. No. 5,087,445, issued to Haffey et al. on Feb. 11, 1992; U.S. Pat. No. 5,073,372, issued to Turner et al. on Dec. 17, 1991; and Chapter VIII of *Cosmetics and Science and Technology* by Segarin et al., pages 189 et seq. (1957), all of which are incorporated herein by reference in their entirety.

Further highly preferred sunscreens which may be formulated into the compositions of the instant invention are those selected from among: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazolylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N, N, N-trimethyl-4-(2-oxoborn-3-ylidene methyl)anillinium methyl sulfate, and mixtures thereof.

Additional sunscreens that can be used herein are described in pages 2954–2955 of the *International Cosmetic Ingredient Dictionary and Handbook* (9$^{th}$ ed. 2002).

The sunscreens are generally present in the compositions according to the invention in proportions ranging from 0.1 to 30% by weight with respect to the total weight of the composition and preferably ranging from 0.2 to 15% by weight with respect to the total weight of the composition. Compositions of the invention preferably have a SPF of 30 and above, including 35, 40, 45, etc.

The present invention compositions containing at least one sunscreen also contain at least one silicone-polyamide copolymer, preferably a Nylon-611/dimethicone copolymer and, in addition, preferably but optionally comprise PPG-3 myristyl ether, for example in an amount ranging from 0–15% by weight based on the total weight of copolymer and myristyl ether. Silicone-polyamide copolymers useful herein include those described in U.S. Pat. Nos. 6,451,295, 6,353,076 and 6,051,216 and WO 99/06473, all of which are incorporated herein by reference. In a highly-preferred embodiment, the compositions of the present invention contain at least one copolymer of the formula:

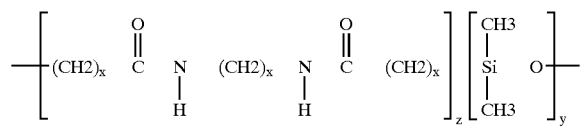

where x is preferably 1–40, and the ratio of y/z ranges from 0.001 to 1000, preferably 1–10, including 2, 3, 4, 5, 6, 7, 8, and 9 and all values and subranges therebetween, said copolymer preferably having a molecular weight of 35,000–200,000 daltons, more preferably 65,000–140,000 daltons, a melt viscosity of 300–7,500 cP, more preferably 750–5000 cP. In a highly preferred embodiment the invention composition comprises Dow Corning® (DC) 2-8178 Gellant (a Nylon-611/dimethicone copolymer).

The amount of silicone-polyamide copolymer used in the invention composition is not particularly limited, and may range from, for example, 0.1–25% by weight and more based on total weight of the composition, preferably 0.5–10% including 2, 3, 4, 5, 6, 7, 8, and 9% and all values and subranges therebetween. In a preferred embodiment the silicone-polyamide copolymer is present in an amount that increases the SPF of the composition by at least 30%, more preferably at least 35, 40, 45, 50, 55, 60, 65, 75, 80, etc. percent, as compared to the composition's SPF without said copolymer. The amount of copolymer may be varied depending upon the form of the invention composition desired which, in view of this disclosure, is within the skill of the ordinary artisan.

Similarly, the amount of PPG-3 myristyl ether, if present, is not particularly limited and may range from, for example, 0.0–25% by weight based on total weight. As noted above the amount of myristyl ether preferably ranges from 0–15% by weight based on the total weight of copolymer and myristyl ether. The preferred material has the formula:

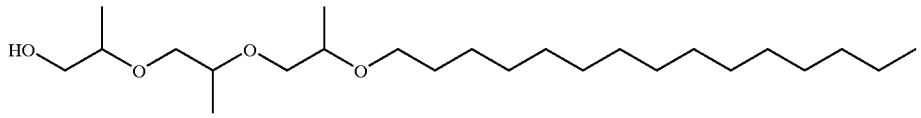

In a highly preferred embodiment of the invention the compositions described herein can comprise, instead of the above-described silicone-polyamide copolymers or in addition thereto, a preferred set of polymers referred to as structuring agents hereinafter, including polymers of the polyorganosiloxane type such as those described in documents U.S. Pat. Nos. 5,874,069, 5,919,441, 6,051,216, and 5,981,680, all incorporated herein by reference.

The structuring polymers to which the invention applies are solids that may be dissolved beforehand in a solvent with hydrogen interaction capable of breaking the hydrogen interactions of the polymers, for instance $C_2$ to $C_8$ lower alcohols and especially ethanol, n-propanol or isopropanol, before being placed in the presence of the silicone oils according to the invention. It is also possible to use these hydrogen interaction "breaking" solvents as co-solvents. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

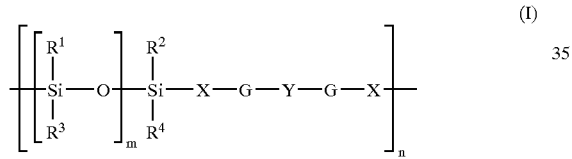
(I)

in which:
1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms:

fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, C, to $C_3$ hydroxyalkyl and $C_1$ to $C_6$ aminoalkyl, or 4) Y represents a group corresponding to the formula:

in which
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
$R^5$ represents a linear or branched $C_1$ to $C_{50}$ alkyl group or a polyorganosiloxane chain, possibly comprising one or more ester, amide, urethane, thiocarbamate, urea, urethane, thiourea and/or sulphonamide groups, which may be linked to another chain of the polymer;

5) the groups G, which may be identical or different, represent divalent groups chosen from:

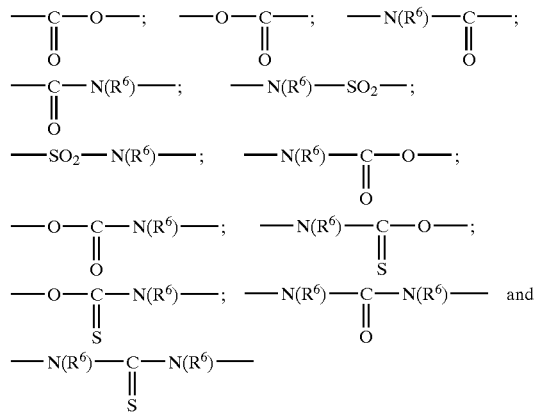

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

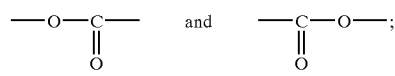

6) n is an integer ranging from 2 to 500 and preferably from 2 to 200, and m is an integer ranging from 1 to 1000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups,
b) $C_{30}$ to $C_{56}$ branched alkylene groups possibly comprising rings and unconjugated unsaturations,
c) $C_5$-$C_6$ cycloalkylene groups,
d) phenylene groups optionally substituted with one or more $C_1$ to $C_{40}$ alkyl groups,
e) $C_1$ to $C_{20}$ alkylene groups comprising from 1 to 5 amide groups,
f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

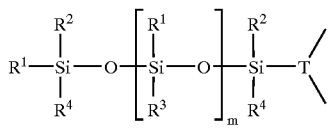

in which $R^1$, $R^2$, $R^3$, $R^4$, T and m are as defined above, and
h) polyorganosiloxane chains of formula:

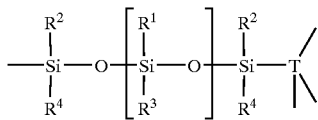

in which $R^1$, $R^2$, $R^3$, $R^4$, T and m are as defined above.

The polyorganosiloxanes of the second family may be polymers comprising at least one moiety corresponding to formula (II):

(II)

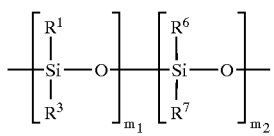

in which
  $R^1$ and $R^3$, which may be identical or different, are as defined above for formula (I),
  $R^7$ represents a group as defined above for $R^1$ and $R^3$, or represents a group of formula —X—G—$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups,
  $R^8$ represents a group of formula —X—G—$R^9$ in which X, G and $R^9$ are as defined above,
  $m_1$ is an integer ranging from 1 to 998, and
  $M_2$ is an integer ranging from 2 to 500.

According to the invention, the polymer used as structuring agent may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea, urethane, thiourea oxamido, guanamido and biguanidino groups, and combinations thereof.

These copolymers may be block copolymers or grafted copolymers. According to a first embodiment of the invention, the groups capable of establishing hydrogen interactions are amide groups of formulae —C(O)NH— and —HN—C(O)—.

In this case, the structuring agent may be a polymer comprising at least one moiety of formula (III) or (IV):

(III)

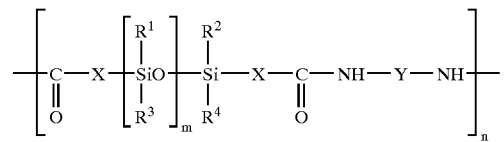

or (IV)

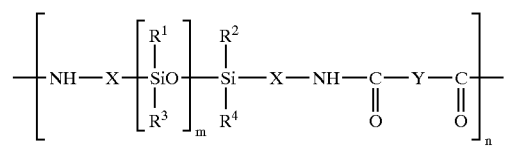

in which $R^1$, $R^2$, $R^3$, $R^4$, X, Y, m and n are as defined above.

Such a moiety may be obtained:
  either by a condensation reaction between a silicone containing, ω-carboxylic acid ends and one or more diamines, according to the following reaction scheme:

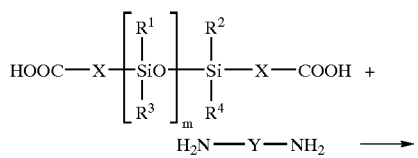

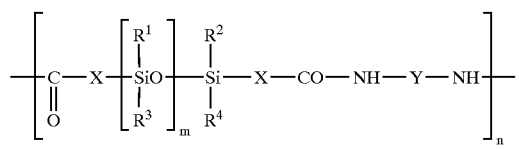

or by reaction of two molecules of -u n saturated carboxylic acid with a diamine according to the following reaction scheme:

$$CH_2=CH-X^1-COOH+H_2N-Y-NH_2 \rightarrow$$

$$CH_2=CH-X^1-CO-NH-Y-NH-CO-X^1-CH=CH_2$$

followed by the addition of a siloxane to the ethylenic unsaturations, according to the following scheme:

$$CH_2=CH-X^1-CO-NH-Y-NH-CO-X^1-CH=CH_2$$

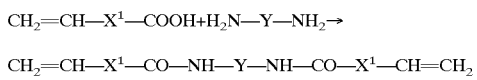

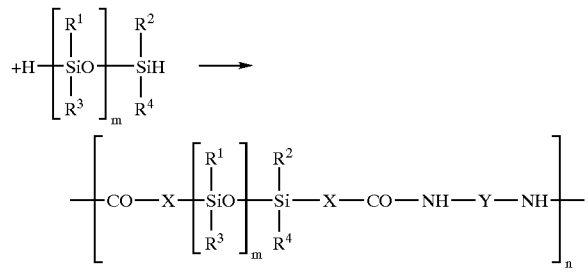

in which $X^1$—$(CH_2)_2$— corresponds to X defined above and Y, $R^1$, $R^2$, $R^3$, $R^4$ and m are as defined above;

or by reaction of a silicone containing, ω-N $H_2$ ends and a diacid of formula HOOC—Y—COOH according to the following reaction scheme:

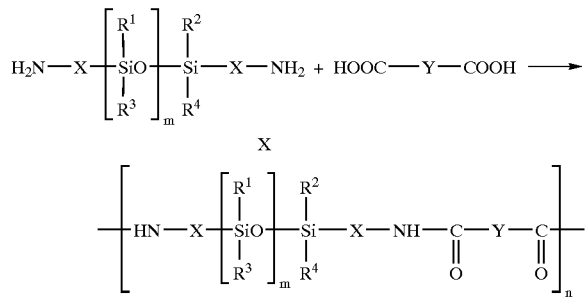

In these polyamides of formula (III) or (IV), m is preferably in the range from 1 to 700, more preferably from 15 to 500 and better still from 15 to 45, and n is in particular in the range from 1 to 500, preferably from 1 to 100 and better still from 4 to 25, X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1°) 1 to 5 amide, urea or carbamate groups,

2°) a $C_5$ or $C_6$ cycloalkyl group, and

3°) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

In these formulae (III) and (IV), Y may also represent:

in which $R^5$ represents a polyorganositoxane chain and T represents a group of formula:

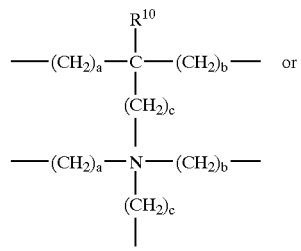

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

(V)

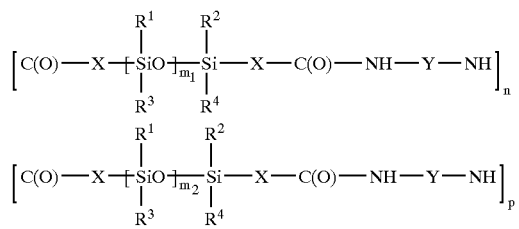

in which X, Y, n and $R^1$ to $R^4$ have the meanings given above, $m_1$ and $m_2$, which are different, are chosen in the range from 1 to 1000, and p is an integer ranging from 2 to 300. In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

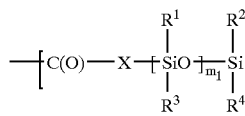 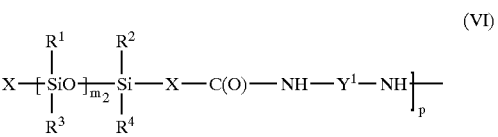

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In this first embodiment of the invention, the structuring polymer may also consist of a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

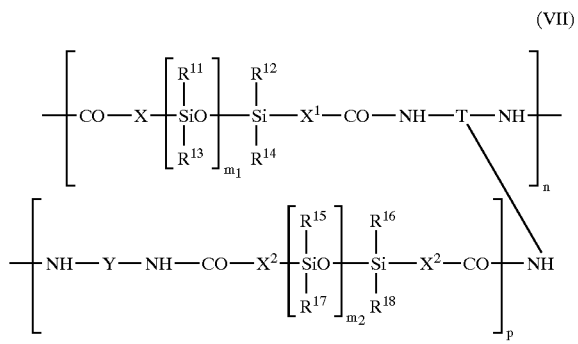

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1000, and p is an integer ranging from 2 to 500. In formula (VII), it is preferred that:

p is in the range from 1 to 25 and better still from 1 to 7, $R^{11}$ to $R^{18}$ are methyl groups, T corresponds to one of the following formulae:

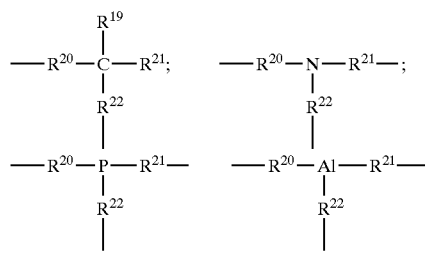

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

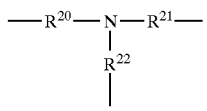

in particular with $R^{20}$, $R^{21}$ and $R^{22}$ representing —$CH_2$—$CH_2$—, $m^1$ and $m_2$ are in the range from 15 to 500 and better still from 15 to 45, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 50;
mixtures of two or more polyamides in which at least one polyamide has a value of m in the range from 15 to 50 and at least one polyamide has a value of m in the range from 30 to 50;
polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;
mixtures of polyamide of formula (III) combining
1) 80% to 99% by weight of a polyamide in which n is equal to 2 to 10 and in particular 3 to 6, and
2) 1% to 20% of a polyamide in which n is in the range from 5 to 500 and in particular from 6 to 100;
polyamides corresponding to formula (VI) in which at least one of the groups Y and $Y^1$ contains at least one hydroxyl substituent;
polyamides of formula (III) synthesized with at least one portion of an activated diacid (diacid chloride, dianhydride or diester) instead of the diacid;
polyamides of formula (III) in which X represents —$(CH_2)_3$— or —$(CH_2)_{10}$; and
polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:
- a $C_1$ to $C_{50}$ alkyl ester group by introducing a $C_1$ to $C_{50}$ monoalcohol during the synthesis,
- a $C_1$ to $C_{50}$ alkylamide group by taking as stopping group a monoacid if the silicone is, ω-diaminated, or a monoamine if the silicone is an, ω-di carboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based structuring agents containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a structuring polymer based on a copolymer between a hydrocarbon-based polyamide and a silicone polyamide, by transamidation of a polyamide having, for example, an ethylene-diamine constituent, with an oligosiloxane-, ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:
- by hydrosilylation of unsaturated bonds in polyamides based on fatty acid dimers;
- by silylation of the amide groups of a polyamide; or
- by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to a second embodiment of the invention, the structuring polymer consists of a homopolymer or a copolymer comprising urethane or urea groups.

As previously, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

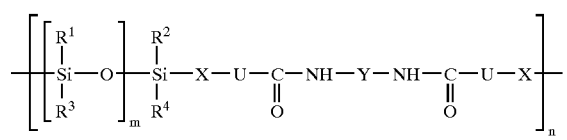

(VIII)

in which $R^1$, $R^2$, $R^3$, $R^4$, X, Y, m and n have the meanings given above for formula (I), and U represents —O— or —NH—, such that:

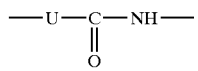

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —(CH$_2$)$_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

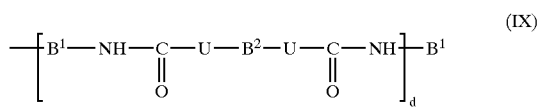
(IX)

in which $B^1$ is a group chosen from the groups given above for Y, U is —O— or —NH— and $B^2$ is chosen from:

- linear or branched $C_1$ to $C_{40}$ alkylene groups, which can optionally bear an ionizable group such as a carboxylic acid or sulphonic acid group, or a neutralizable or quaternizable tertiary amine group,
- $C_5$ to $C_{12}$ cycloalkylene groups, optionally bearing alkyl substituents, for example one to three methyl or ethyl groups, or alkylene, for example the diol radical: cyclohexanedimethanol,
- phenylene groups that may optionally bear $C_1$ to $C_3$ alkyl substituents, and
- groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

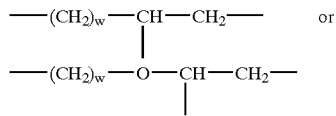

with w being an integer ranging from 1 to 10 and $R^5$ being a polyorganosiloxane chain. When Y is a linear or branched $C_1$ to $C_{40}$ alkylene group, the —(CH$_2$)$_2$— and —(CH$_2$)$_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —(CH$_2$)$_2$— or —(CH$_2$)$_6$— or a group:

with $R^5$ being a polyorganosiloxane chain.

As previously, the structuring polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

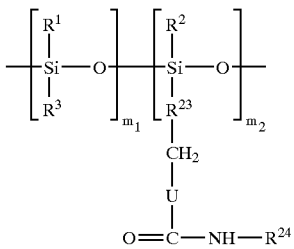
(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as structuring agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

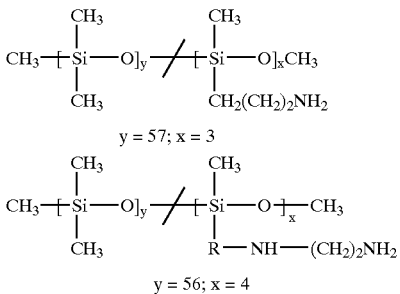

y = 57; x = 3 y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

The polymers of formula (VIII) comprising urea or urethane groups in the chain of the silicone polymer may be obtained by reaction between a silicone containing, ω-NH$_2$ or —OH end groups, of formula:

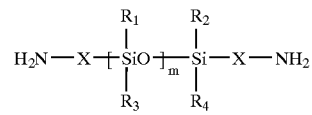

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula H$_2$N—B$^2$—NH$_2$ or HO—B$^2$—OH, in which B$^2$ is as defined in formula (IX).

According to the stoichiometric proportions between the two reagents, diisocyanate and coupling agent, Y may have the formula (IX) with d equal to 0 or d equal to 1 to 5.

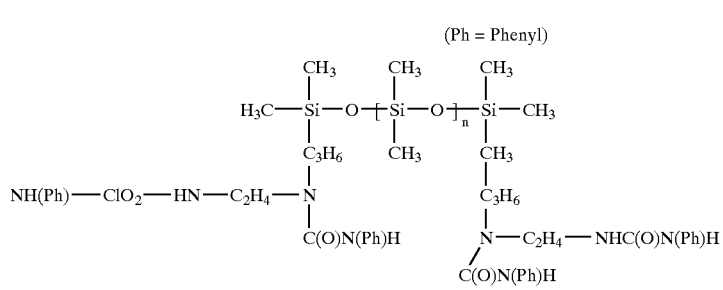

(XI)

in which Ph is a phenyl group and n is a number from 0 to 300, in particular from 0 to 100, for example 50.

This polymer is obtained by reacting the following polysiloxane containing amino groups:

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

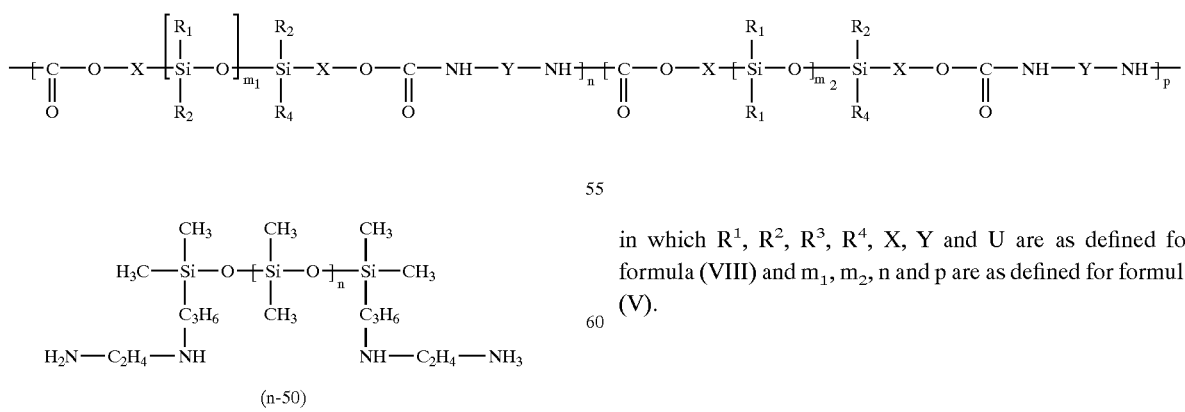

(XII)

in which $R^1$, $R^2$, $R^3$, $R^4$, X, Y and U are as defined for formula (VIII) and m$_1$, m$_2$, n and p are as defined for formula (V).

with phenyl isocyanate.

Branched polyurethane or polyurea silicones may also be obtained using, instead of the diisocyanate OCN—Y—NCO, a triisocyanate of formula:

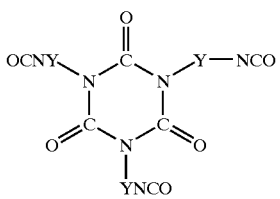

A polyurethane or polyurea silicone containing branches comprising an organosiloxane chain with groups capable of establishing hydrogen interactions is thus obtained. Such a polymer comprises, for example, a moiety corresponding to the formula:

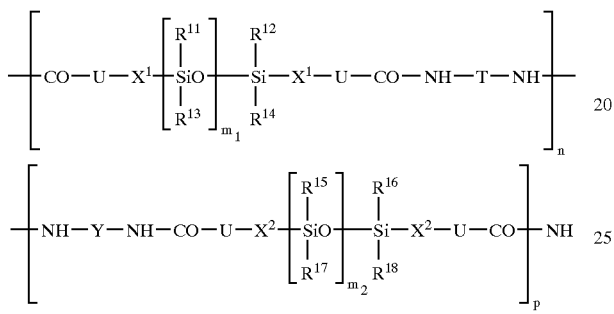

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1000, and p is an integer ranging from 2 to 500.

As in the case of the polyamides, this copolymer can also comprise polyurethane silicone moieties without branching.

In this second embodiment of the invention, the siloxane-based polyureas and polyurethanes that are preferred are:

polymers of formula (VIII) in which m is from 15 to 50;

mixtures of two or more polymers in which at least one polymer has a value of m in the range from 15 to 50 and at least one polymer has a value of m in the range from 30 to 50;

polymers of formula (XII) with m1 chosen in the range from 15 to 50 and $m_2$ chosen in the range from 30 to 500 with the portion corresponding to m1 representing 1% to 99% by weight of the total weight of the polymer and the portion corresponding to $m_2$ representing 1% to 99% by weight of the total weight of the polymer;

mixtures of polymer of formula (VIII) combining
1) 80% to 99% by weight of a polymer in which n is equal to 2 to 10 and in particular 3 to 6, and
2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an, ω-di functional block of non-silicone nature, for example a polyester, a polyether or a polyolefin.

As has been seen previously, the structuring polymer consisting of homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

(1)

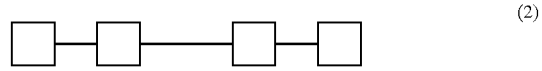

(2)

(3)

(4)

(5)

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

According to the invention, the structuring of the liquid fatty phase containing at least one silicone oil is obtained with the aid of one or more of the polymers mentioned above, in combination with solid particles with a hydrophobic surface.

As examples of polymers that may be used, mention may be made of the silicone polyamides obtained in accordance with Examples 1 and 2 of document U.S. Pat. No. 5,981,680

The compositions according to the invention are preferably intended for topical application to the skin and/or its superficial body growths and therefore preferably comprise a physiologically acceptable medium, that is to say a medium compatible with cutaneous tissues, such as the skin, scalp, eyelashes, eyebrows, hair, nails and mucous membranes. This physiologically acceptable medium may comprise an aqueous phase and optionally a physiologically acceptable organic solvent chosen, for example, from lower alcohols comprising from 1 to 8 carbon atoms and in particular from 1 to 6 carbon atoms, such as ethanol, isopropanol, propanol or butanol; polyethylene glycols having from 6 to 80 ethylene oxide units; or polyols, such as propylene glycol, isoprene glycol, butylene glycol, glycerol or sorbitol. When the physiologically acceptable medium is an aqueous medium, it generally preferably has a pH which is compatible with the skin, preferably ranging from 3 to 9 and better still from 3.5 to 7.5.

As noted above, the compositions according to the invention can be provided in any form, including any form used conventionally for topical application and in particular in the form of aqueous or aqueous/alcoholic gels, aqueous or aqueous/alcoholic solutions, of oil-in-water (O/W) or water-in-oil (W/O) or multiple (triple: W/O/W or O/W/O) emulsions, of dispersions of a fatty phase in an aqueous phase using spherules, it being possible for these spherules to be polymeric nanoparticles, such as nanospheres and nanocapsules, or lipid vesicles of ionic and/or nonionic type (liposomes, niosomes or oleosomes). In addition, the invention composition may be anhydrous. These invention forms may be prepared according to methods known to those of ordinary skill in the art in view of this disclosure.

In addition, the compositions according to the invention can be more or less fluid and can have the appearance of a white or coloured cream, of an ointment, of a milk, of a lotion, of a serum, of a paste, a gel or of a foam, for example. In a highly preferred embodiment the invention composition is clear, and particularly a clear gel. Also highly preferred is an aqueous/alcoholic clear gel. The compositions according to the invention can optionally be applied to the skin in the form of an aerosol. They can also be provided in a solid form, for example in the form of a stick.

The compositions of the invention can also comprise adjuvants, for example those known in the cosmetics or dermatological field, such as hydrophilic or lipophilic gelling agents, preservatives, solvents, fragrances, fillers, bactericides, odour absorbers, colouring materials, plant extracts or salts, for example. The amounts of these various adjuvants are those used in the field under consideration, for example from 0.01 to 20% of the total weight of the composition. These adjuvants, depending on their nature, can be introduced into the fatty phase, into the aqueous phase and/or into the lipid spherules.

Mention may be made, as fillers which can be used in the composition of the invention, for example, of pigments, silica powder; talc; particles of polyamide and in particular those sold under the name Orgasol by Atochem; polyethylene powders; microspheres based on acrylic copolymers, such as those made of ethylene glycol dimethacrylate/lauryl methacrylate copolymer which are sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; and their mixtures. These fillers can be present in amounts ranging from 0 to 20% by weight and preferably from 1 to 10% by weight with respect to the total weight of the composition.

The following Examples illustrate various aspects and preferred embodiments of the invention, but are not limiting in any way.

EXAMPLES

Example 1

| ALCOHOLIC CLEAR GEL CONTAINING DC 2-8178 GELLANT | | |
|---|---|---|
| Phase | Chemical Name | % wt/wt |
| A-1 | SD-Alc 40-2 | 64.000 |
| | Octyldodecyl Neopentanoate | 5.000 |
| | C12–15 Alkyl benzoate | 3.000 |
| | Avobenzone | 3.000 |
| | Octocrylene | 10.000 |
| | Benzophenone-3 | 6.000 |
| | Octyl Salicylate | 5.000 |
| A-2 | DC 2-8178 Gellant * | 2.000 |
| A-3 | Hydroxy Propyl Cellulose | 2.000 |

* 88% solid silicone polyamide in 12% PPG-3 myristyl ether

Procedure:
1) Weigh components of Phase A-1 into a beaker
2) Mix using overhead stirring mixture until all components are dissolved into SD-Alc 40-2.
3) Add a component of Phase A-2 into a Phase A-1. Mix until dissolve.
4) Slowly add a component of Phase A-3 into above mixture. Increase a stirring rate and continue mixing for 1.5 to 2.0 hours.

Example 2

Comparison of Composition's SPF

Several sunscreen gels were prepared. Sunscreen Gel 1 was prepared without a film former, while sunscreen Gels 2–5 were prepared with the film formers indicated in the table below. These sunscreen gels were measured and their SPF results are presented below:

| Summary of SPF Analysis | | |
|---|---|---|
| Product | SPF (invitro) | Result |
| 1) Sunscreen Gel without film former | 1) 22.99  2) 21.37 | Avg. 22.18 |
| 2) Sunscreen Gel with 2% Dermacryl LT | 1) 28.3  2) 24.7 | Avg. 26.5 |
| 3) Sunscreen Gel with 2% Dermacryl 79 | 1) 28.18  2) 28.48 | Avg. 28.33 |
| 4) Sunscreen Gel with 2% PPG-12/SMDI Copolymer | 1) 28.55  2) 28.03 | Avg. 28.29 |
| 5) Sunscreen Gel with 2% DC Gellant 2-8178 | 1) 36.32  2) 35.99 | Avg. 36.16 |

DC Gellant 2-8178, Dermacryl LT, Dermacryl 79, and PPG-12/SMDI Copolymer are more fully described in their product brochures, MSDS sheets, etc.

As demonstrated by the results in the above Table, Gel 5 shows a 63% increase in SPF as compared to Gel 1 [((36.16/22.18)−1)×100%].

In view of the above description of the invention, one of ordinary skill in the art is enabled to both make and use a composition comprising a sunscreen and a silicone-polyamide copolymer, including a composition wherein said copolymer is a nylon-611/dimethicone copolymer as well as a composition further comprising PPG-3 myristyl ether. As noted, the invention compositions fully described herein preferably have the copolymer present in an amount that increases the SPF of the composition by at least 30% as compared to the same composition not containing said copolymer. Also fully described such that one of ordinary skill in the art can make and use it is a method of increasing the SPF of a sunscreen composition comprising at least one sunscreen, comprising adding to said composition a silicone-polyamide copolymer, where adding means and includes all orders of addition of components. Another such method fully described is a method of preparing a sunscreen composition, comprising mixing at least one sunscreen and at least one silicone-polyamide copolymer, where mixing means and includes all orders of addition and contact of components.

All references, texts, patents, patent applications, product literature, product brochures and MSDS sheets, documents, publications etc., mentioned above are incorporated herein by reference. Where a numeral range or limit is described, all values therewithin are specifically included as if separately written out. For example, the phrase "in an amount that increases by at least 30%, more preferably at least 35, 40, 45, 50, 55, 60, 65, 75, 80, etc. percent, as compared to the composition's SPF without said copolymer" specifically includes 42%, 47.4% and 118%.

What is claimed is:

1. A composition comprising a sunscreen and a SPF-enhancing effective amount of a silicone-polyamide copolymer, wherein said copolymer is a nylon-611/dimethicone copolymer.

2. The composition according to claim 1, further comprising PPG-3 myristyl ether.

3. The composition according to claim 1, wherein said copolymer is present in an amount that increases the SPF of the composition by at least 30% as compared to the same composition not containing said copolymer.

4. The composition according to claim 1, further comprising at least one alcohol.

5. The composition according to claim 1, wherein said composition is in the form of an emulsion.

6. The composition according to claim 1, wherein said composition is in the form of a gel.

7. The composition according to claim 4, wherein said composition is in the form of a gel.

8. A method of increasing the SPF of a sunscreen composition comprising at least one sunscreen, comprising adding to said composition a silicone-polyamide copolymer.

9. The method according to claim 8, wherein the silicone-polyamide is a nylon-611/dimethicone copolymer.

10. The method according to claim 8, wherein the silicone-polyamide is a silicone-polyamide copolymer of the formula:

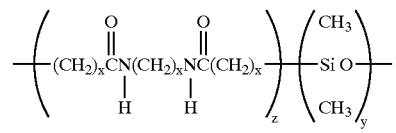

where x is 1–40, the ratio of y/z ranges from 0.001 to 1000, said copolymer having a molecular weight of 35,000–200,000 daltons and a melt viscosity of 300–7,500 cP.

11. The method according to claim 8, wherein said copolymer is present in an amount that increases the SPF of the composition by at least 30% as compared to the same composition not containing said copolymer.

12. The method according to claim 9, wherein said copolymer is present in an amount that increases the SPF of the composition by at least 30% as compared to the same composition not containing said copolymer.

13. The method according to claim 10, wherein said copolymer is present in an amount that increases the SPF of the composition by at least 30% as compared to the same composition not containing said copolymer.

14. The method according to claim 8, wherein said composition further comprises at least one alcohol.

15. The method according to claim 8, wherein said composition is in the form of an emulsion.

16. The method according to claim 8, wherein said composition is in the form of a gel.

17. The method according to claim 8, wherein said composition further comprises PPG-3 myristyl ether.

18. The method according to claim 9, wherein said composition further comprises PPG-3 myristyl ether.

* * * * *